United States Patent
Ohshika et al.

(10) Patent No.: US 7,931,894 B2
(45) Date of Patent: Apr. 26, 2011

(54) METHOD OF THREE-DIMENSIONALLY CULTURING CHONDROCYTES

(75) Inventors: Shusa Ohshika, Hirosaki (JP); Keiichi Takagaki, Hirosaki (JP); Yoko Takagaki, legal representative, Hirosaki (JP); Yasuyuki Ishibashi, Hirosaki (JP); Satoshi Toh, Hirosaki (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 815 days.

(21) Appl. No.: 11/658,744

(22) PCT Filed: Jun. 1, 2005

(86) PCT No.: PCT/JP2005/010038
§ 371 (c)(1),
(2), (4) Date: Jan. 29, 2007

(87) PCT Pub. No.: WO2006/011296
PCT Pub. Date: Feb. 2, 2006

(65) Prior Publication Data
US 2009/0004151 A1    Jan. 1, 2009

(30) Foreign Application Priority Data
Jul. 30, 2004  (JP) .................. 2004-223616

(51) Int. Cl.
A61K 35/32   (2006.01)
C12N 11/04   (2006.01)
C12N 5/077   (2006.01)

(52) U.S. Cl. ........ 424/93.7; 435/325; 435/182; 435/395

(58) Field of Classification Search .............. 424/93.7; 435/182, 325, 395
See application file for complete search history.

(56) References Cited

U.S. PATENT DOCUMENTS

| | | | |
|---|---|---|---|
| 6,197,061 B1 * | 3/2001 | Masuda et al. | 623/11.11 |
| 6,444,222 B1 * | 9/2002 | Asculai et al. | 424/484 |
| 2003/0040113 A1 * | 2/2003 | Mizuno et al. | 435/395 |
| 2004/0151705 A1 * | 8/2004 | Mizuno et al. | 424/93.7 |

FOREIGN PATENT DOCUMENTS
WO    WO 03/084385 A2    10/2003

OTHER PUBLICATIONS

Zhu et al. 1996. Determination of Collagen-Proteoglycan Interactions In Vitro. J. Biomechanic. 29(6):773-783.*
Ohshika, et al., Effect of Cartilage-Derived Proteoglycan on Proliferation and Phenotype Expression of Cultured Chondrocytes Embedded in Collagen Gel, Connect Tissue, vol. 36, No. 2, Jun. 2004, p. 88.
Schuman, et al., Chondrocyte Behaviour Within Different Types of Collagen Gel in Vitro, Biomaterials, vol. 16, No. 10, 1995, pp. 809-814.
Chaipinyo, et al., Effects of Growth Factors on Cell Proliferation and Matrix Synthesis of Low-Density, Primary Bovine Chondrocytes Cultured in Collagen I Gels, Journal of Orthopaedic Research, vol. 20, No. 5, Sep. 2002, pp. 1070-1078.
French, et al., Expression of the Heparan Sulfate Proteoglycan, Perlecan, during Mouse Embryogenesis and Perlecan Chondrogenic Activity in Vitro, Journal of Cell Biology, vol. 145, No. 5, May 31, 1999, pp. 1103-1115.
Knudson, et al., Cartilage Proteoglycans, Seminars in Cell & Developmental Biology, vol. 12, 2001, pp. 69-78.
Ohshika, et al., Effect of Exogenous Proteoglycan on Cultured Chondrocyte, Proteoglycan, vol. 76, No. 8, Aug. 25, 2004, p. 1009.
Arikawa-Hirasawa, et al., Perlecan is Essential for Cartilage and Cephalic Development, Nature Genetics, vol. 23, Nov. 1999, pp. 354-358.

* cited by examiner

*Primary Examiner* — Taeyoon Kim
(74) *Attorney, Agent, or Firm* — Sughrue Mion, PLLC

(57)    ABSTRACT

It is intended to provide a method of three-dimensionally culturing normal joint chondrocytes; the production and supply of chondrocytes; and a transplantation material to be used in an injured site in a joint tissue.

2 Claims, 5 Drawing Sheets

-a

-b

-c

-a

-b

-c

-a

-b

-c

METHOD OF THREE-DIMENSIONALLY CULTURING CHONDROCYTES

This Application is a 371 of PCT/JP2005/010038, filed Jun 1, 2005; the disclosure of which is incorporated herein by reference.

TECHNICAL FIELD

The present invention mainly relates to a method of producing chondrocytes, and to providing a transplantation material to an injured site in a cartilage tissue. The present invention also relates to a kit for studying the cartilage tissue.

BACKGROUND TECHNOLOGY

When a damage or a defect occurs in a joint cartilage due to some cause, it is rare that the joint cartilage is completely restored and regenerated. One of the reasons includes a nature of chondrocyte. That is, as the joint chondrocytes are highly differentiated, scarcely proliferate and differentiate, their restoration capacity is extremely low. Another reason includes a peripheral inherent environment surrounding the chondrocytes. Since a cartilage tissue lacks a nerve and a blood vessel, no restoration mechanism by hemorrhage, inflammation and granulation is available. Since a periphery of the cartilage tissue is surrounded by extracellular matrix, the chondrocytes can not easily migrate from a healthy site to the injured site.

The injured site in the joint cartilage induces degradation of its periphery and adjacent cartilage with time, finally advances to osteoarthritis, and causes the reduction of joint functions, e.g., pain and mobile limitation. Therefore, various therapeutic methods have been developed as methods of restoring the joint cartilage so far, but this is an actual state that the method of restoring a defect site with complete hyaline cartilage has not been well established at present.

Accompanying with the recent advance of cell engineering, regeneration of the cartilage tissue by autologous chondrocytes has been actively attempted. It is important as a transplantation material applied to the injured site that enough amount of the chondrocytes are maintained, and that the retained chondrocytes can produce the sufficient amount of the extracellular matrix.

However, there is a problem that the chondrocytes dedifferentiate into fibroblasts during the culture when the chondrocytes are isolated from an autologous cartilage piece and subsequently grown in a monolayer culture. Thus, it is difficult to culture the chondrocytes keeping with their character well. As a scaffolding exhibiting a three dimensional structure, biomaterials such as collagen gel sponge, agarose gel, gelatin, chitosan, hyaluronic acid and PGA, PLA and PLGA have been reported, but no material having strength and frictional coefficient corresponding to a cartilage matrix has been developed until now, and a transplantation material having the characters close to the joint cartilage tissue has been desired.

DISCLOSURE OF INVENTION

Problem to be Solved By The Invention

It is an object of the present invention to provide a method of culturing chondrocytes and a transplantation material for regeneration of a cartilage tissue in an injured site in the cartilage tissue based on this method, and a kit for studying the cartilage tissue.

Means For Solving The Problem

As a result of an extensive study in such an actual circumstance, the present inventors have found that normal chondrocyte can be grown in a gelled-structure comprising collagen and proteoglycan with keeping the characters in the absence of various growth factors. The present inventors also have found that cartilage tissue components produced from these chondrocytes reconstruct a new three-dimensional structure similar to the cartilage tissue in the gelled-structure, and provide an ideal transplantation material for regeneration of the cartilage tissue. By further advancing this fact, it is possible to provide a material for studying the cartilage tissue in future.

That is, it is possible to provide the following inventions.

[1] A method for three-dimensional culture of chondrocytes, characterized by culture condition in which the chondrocytes are embedded in a gelled structure comprising collagen and proteoglycan.

[2] The method according to [1] wherein a ratio of collagen to proteoglycan is 1:0.3 to 1.1 (weight ratio).

[3] A method of chondrocyte production characterized in that the chondrocytes are grown in a gelled structure comprising collagen and proteoglycan.

[4] A gelled-structure comprising collagen and proteoglycan that is capable of regenerating a cartilage tissue by embedding the chondrocytes in the gelled-structure.

[5] The gelled-structure according to [4] which is a transplantation material to the injured site in a cartilage tissue.

[6] A kit comprising at least chondrocytes, collagen and proteoglycan for studying a cartilage tissue.

EFFECT OF THE INVENTION

The present invention of three-dimensional chondrocyte culture system made it possibles to grow the cells with keeping their characters as chondrocytes and the resulting material thus obtained can be provided as the caltilage transplantation material.

BEST MODES FOR CARRYING OUT THE INVENTION

Figure 1:
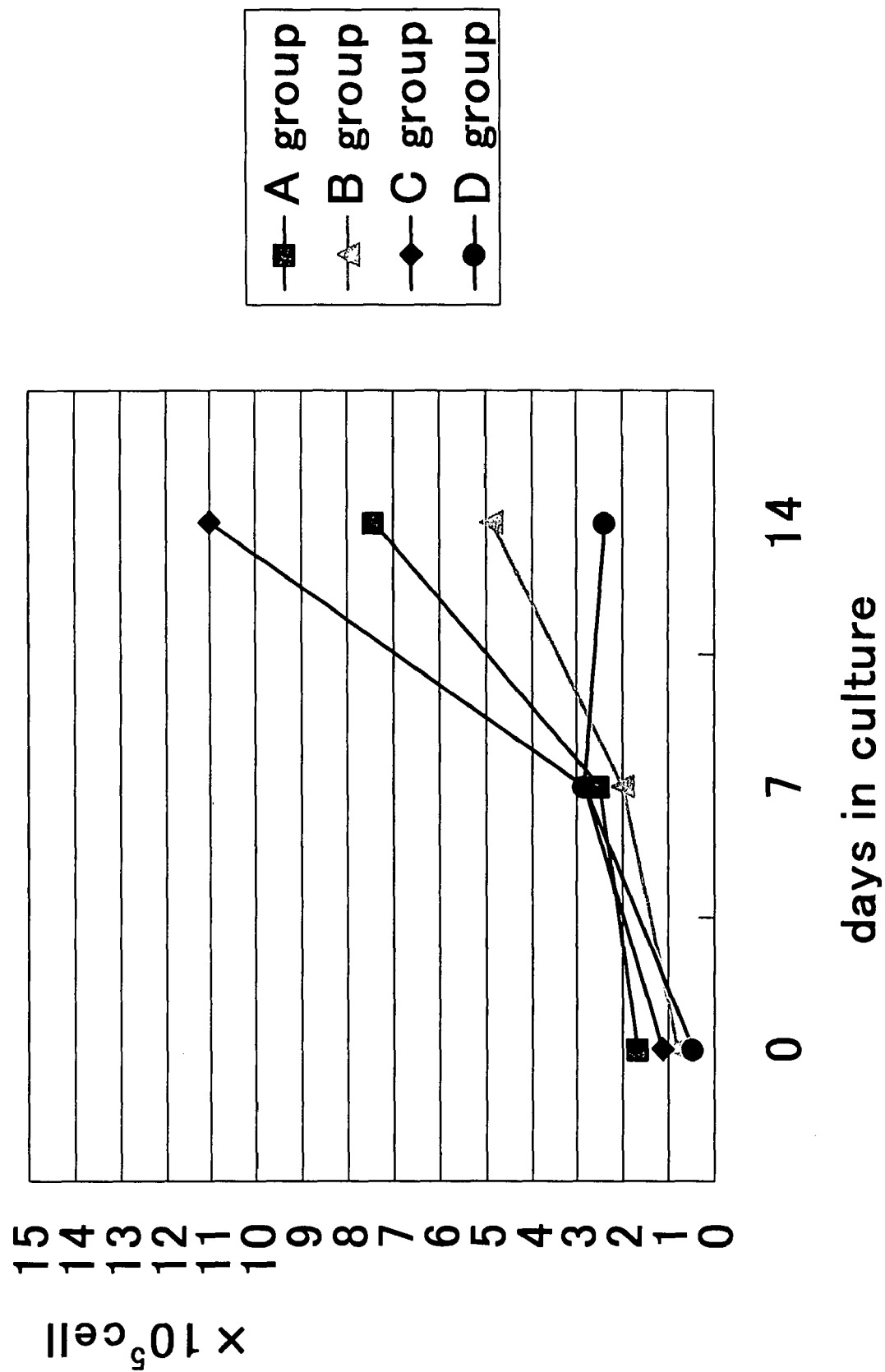
FIG. 1 shows the change of cell numbers when chondrocytes were cultured in a gelled-structure comprising type I atelocollagen and proteoglycan. The ratio of atelocollagen to proteoglycan is A group (1:0), B group (1:0.5), C group (1:0.51) or D group (1:2.56).

In one preferable embodiment of the present invention, as chondrocytes subjected to the present invention, the normal chondrocytes present in a joint tissue can be used, but the chondrocytes obtained from bone marrow cells and mesenchymal stem cells capable of being differentiated and induced into the chondrocytes can be used. Depending on the purpose, the normal chondrocytes derived from human beings and animals other than the human beings can be used.

Collagen (e.g., types II, III, IV, V, VI, VIII, IX, X or mixtures thereof) is not particularly limited, preferably Type I and Type II collagen can be used, and in particular, preferably Type II collagen or a collagen mixture containing Type II collagen can be used.

Collagen is preferably atelocollagen for increasing water solubility, and low molecular weight collagen hydrolyzed with enzyme may be used, if it is possible to form the scaffoldings with maintaining the three-dimensional structure. When the transplantation is subjected to the human being, human-derived collagen is desirable, but collagen is not particularly limited and collagen derived from the animal other than the human being, such as, collagen derived from rabbits, cattle, horses and mice can be suitably used.

The "gelled-structure" or the "three-dimensional structure" herein means one capable of embedding the chondrocytes therein, becoming the scaffoldings of the chondrocytes and making the chondrocytes grow in the structure.

Proteoglycan may be derived from any of the human being and the animals other than the human being, further proteoglycan derived from fishes or the large animal may be used in terms of material collection, and proteoglycan derived from mammalian animals such as rabbits, cattle, horses and mice can be suitably used. In the case of using the fishes, proteoglycan isolated from salmon or shark can be used.

The ratio of collagen to proteoglycan is particularly important to make the chondrocytes grow with keeping the characters of the normal chondrocyte, preferably proteoglycan is in the range of 0.3 to 1.1 relative to 1 of collagen in weight ratio, and more suitably it is preferable that proteoglycan is in the range of about 0.5 to 0.7 relative to 1 of collagen.

As culture media for the chondrocytes, it is possible to use the media and additives used for the ordinary culture of the chondrocytes or the mesenchymal cells without limitation. As the media, for example, RPMI1647, RPMI1640, MEM, BME, 5A, DM120, RITC80-7, F12, L-15, MCDB104 and MCDB107 can be suitably used. Upon culture, it is desirable to add serum, a concentration of the serum can be appropriately selected between 1 to 20% depending on the conditions, and suitably the serum can be used suitably in the range of 5 to 15%, and more suitably in the range of 5 to 10%. As the type of the serum, sera derived from various animals can be used without limitation, for example, bovine serum, fetal calf serum and horse serum can be used.

Collagen and proteoglycan to be used are mixed in the medium at an aforementioned predetermined ratio, and are desirably used in the range of the concentration at which they can be gelled and form the three-dimensional structure. The concentration of collagen is 0.8 to 2.4% by weight and preferably 1.2 to 2.0% by weight, and the concentration of proteoglycan is 0.4 to 1.2% by weight and preferably 0.6 to 1.0% by weight. The total concentration of collagen and proteoglycan is about 1.2 to 3.6% by weight and preferably about 1.8 to 3.0% by weight. When these concentrations are too low, the gel strength becomes insufficient whereas when they are too high, the gel becomes excessively hard and can not keep the sufficient steric structure.

The gelled structure can be completed by adding the chondrocytes to the gel mixed in this way, stirring to become sufficiently homogenous and then by dropping or placing on a culture dish.

To stabilize the structure, it is desirable to leave stand in an incubator for about 10 to 30 minutes after dropping or placing the mixture on the culture dish. Then, the medium is added to an extent that the gelled-structure is submerged and the culture is started. This procedure can be performed according to the collagen drop method (Journal of Hepato-Biliary-Pancreatic Surgery 5(3) 261-268 (1998)), but the method is not always limited thereto. As the chondrocytes to be used, for example, those collected from the injured site in the joint and separated by the standard methods can be used. The number of cells to be used is suitably in the range of about $1 \times 10^3$ to $1 \times 10^6$ cells per mL, and more suitably in the range of about $1 \times 10^4$ to $5 \times 10^5$ cells per mL.

It is appropriate that a culture period is about 2 to 8 weeks, and even if the culture is continued for 8 weeks or more, the cell morphology is kept. Therefore, the culture period can be appropriately determined depending on the number of the chondrocytes added at the start of the culture. Thus, in this culture condition, the chondrocytes proliferate in the gelled structure with keeping their characters. It is preferable to change the medium every 2 to 4 days, which is within the condition under which the ordinary cell culture is performed.

In the joint cartilage tissue, the normal chondrocytes occupy only about 2%, and the propotion of extracellular matrix including collagen and proteoglycan is very high. From this point of view, the presence of the extracellular matrix in the joint tissue is important. In the present culture system, the chondrocytes not only start their proliferation with keeping their characters but also produce the extracellular matrix. That is, the extracellular matrices typically present in the joint tissue, such as type II collagen, a marker of the chondrocyte and proteoglycan are accumulated in the gelled-structure. In this sense, they seem to construct a joint-like tissue. Therefore, it is possible to collect the chondrocytes separately from the culture system, and further the gelled-structure containing the joint-like tissue can also be used as the good transplantation material for the purpose of regenerating the cartilage injury site.

For this regeneration procedure, the joint-like gelled-structure can be transplanted to the injured site by trimming the size and shape adjusting the injured area.

Since the pseudo-cartilage gelled-structure is reconstructed by extracellular matrices such as type II collagen, proteoglycan and fibronectin produced by the normal chondrocytes, this system is excellent to provide the useful material for studying the cartilage tissue. Taken together, it is possible to provide a kit comprising the chondrocytes, collagen and proteoglycan for studying the cartilage tissue.

EXAMPLES

The present invention will be described in more detail with reference to Examples. These Examples are described for the purpose of exemplifications only, and do not limit the present invention.

Example 1

Culture of Chondrocytes

Chondrocytes (purchased from Hokudo Co., Ltd.) isolated from a rabbit knee joint cartilage were used. The chondrocytes obtained after the first passage were used for the experiment. A culture medium RPMI 1640 containing 10% FBS and 100 μM ascorbic acid (Hokudo Co., Ltd.) was used. A mixture containing following ratio, 3% Type I collagen:(proteoglycan+culture medium)=65 μL:60 μL was prepared and the chondrocytes (about $1 \times 10^5$) were added thereto (weight ratios of atelocollagen proteoglycan, A group [1:0], B group [1:0.05], C group [1:0.51] and D group [1:2.56]). Then the mixture was thoroughly stirred, dropped on a 35 mm dish, and gelled by incubating at 37° C. for 10 minutes. After confirming that the gel was formed well, 2.5 mL of the culture medium was added. The cells were cultured in 5% $CO_2$ at 37° C. The medium was changed twice a week, and the culture was performed for 21 days.

In the meantime, the cell number was counted on the 7th and 14th days after the start of the culture in accordance with the procedure described below. That is, the gel was peeled from the dish and transferred to another 35 mm dish. The culture medium and collagenase (collagenase S-1, Nitta gelatin) were added to the dish, which was then incubated at 37° C. for 60 minutes to liberate the cells (FIG. 1). Cell viability was counted using a hemocytometer. The number of the alive cells was confirmed by staining with trypan blue. As a result, the cell numbers in the A to C groups were increased. In D group, the cell number was decreased on the 14th day. Comparing respective groups, the cell number in the C group was obviously higher than that in the other groups.

In the B group, the morphological change to fibroblasts was slightly observed. In the D group, no morphological change was observed, but the proliferation was slow and it was also difficult to maintain the gel.

Histological and Immunohistological Evaluation

Figure 2:
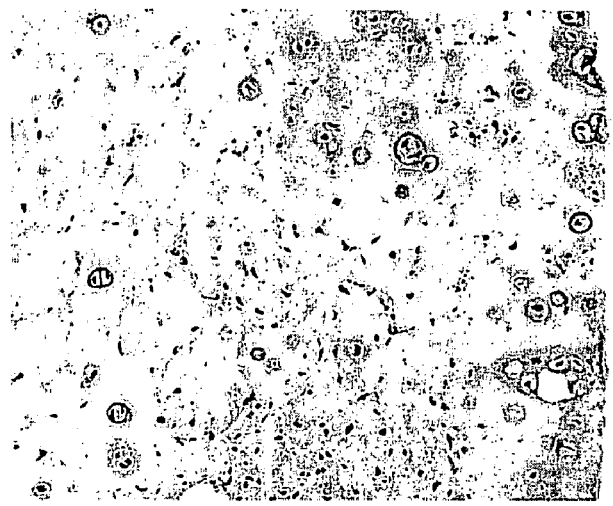
FIG. 2 shows the gelled structure stained with hematoxylin and eosin after the culture. a, b and c represent A group, B group and C group, respectively.
Figure 2:
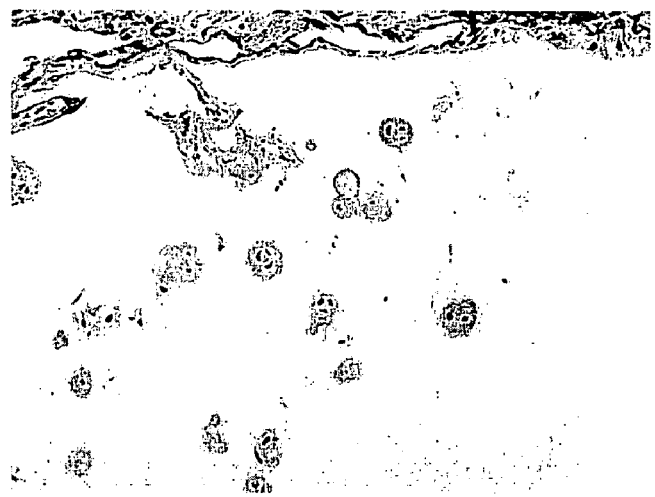
Figure 2:
Figure 3:
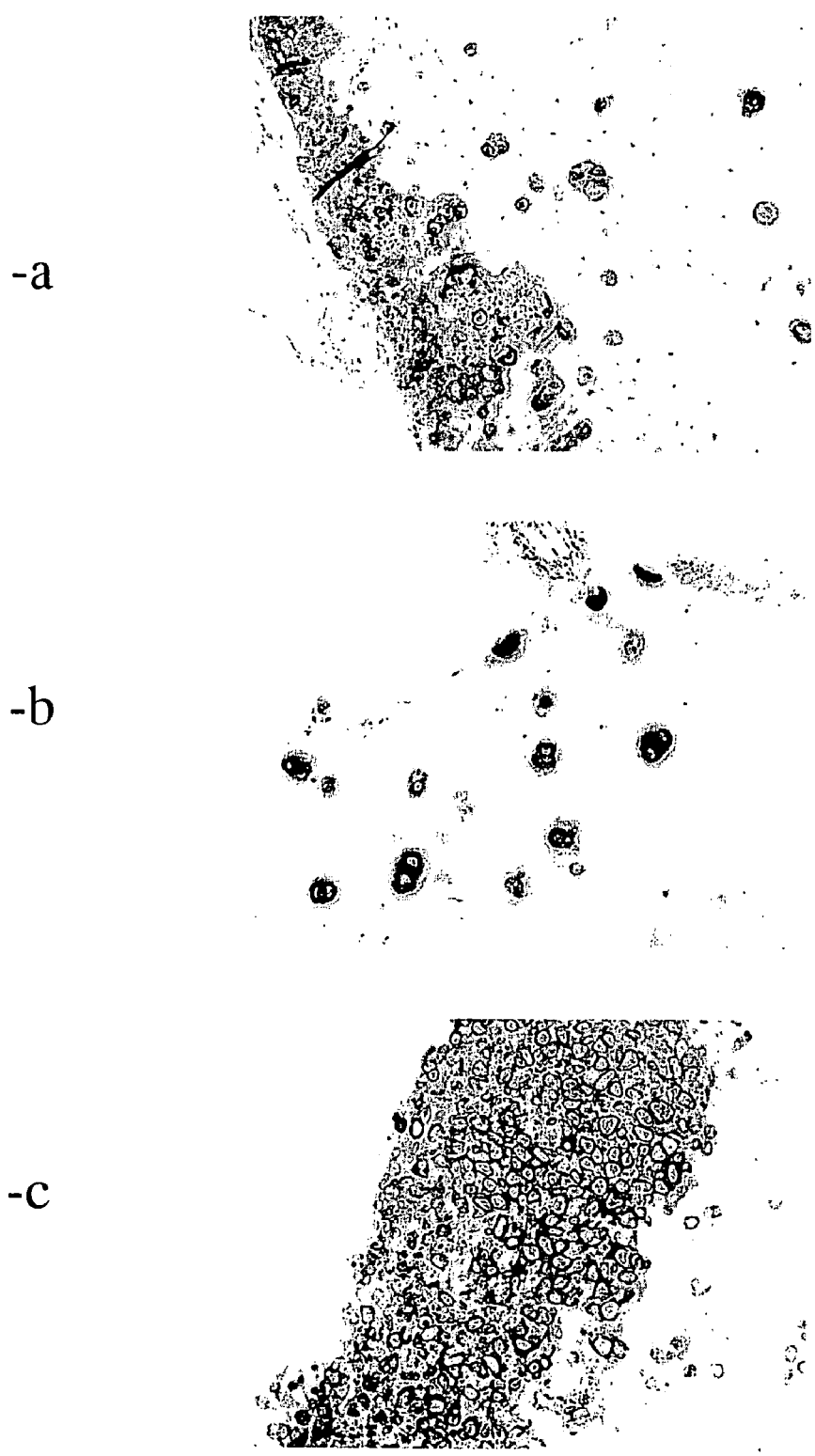
FIG. 3 shows the gelled structure stained with alcian blue after the culture. a, b and c represent A group, B group and C group, respectively.
Figure 4:
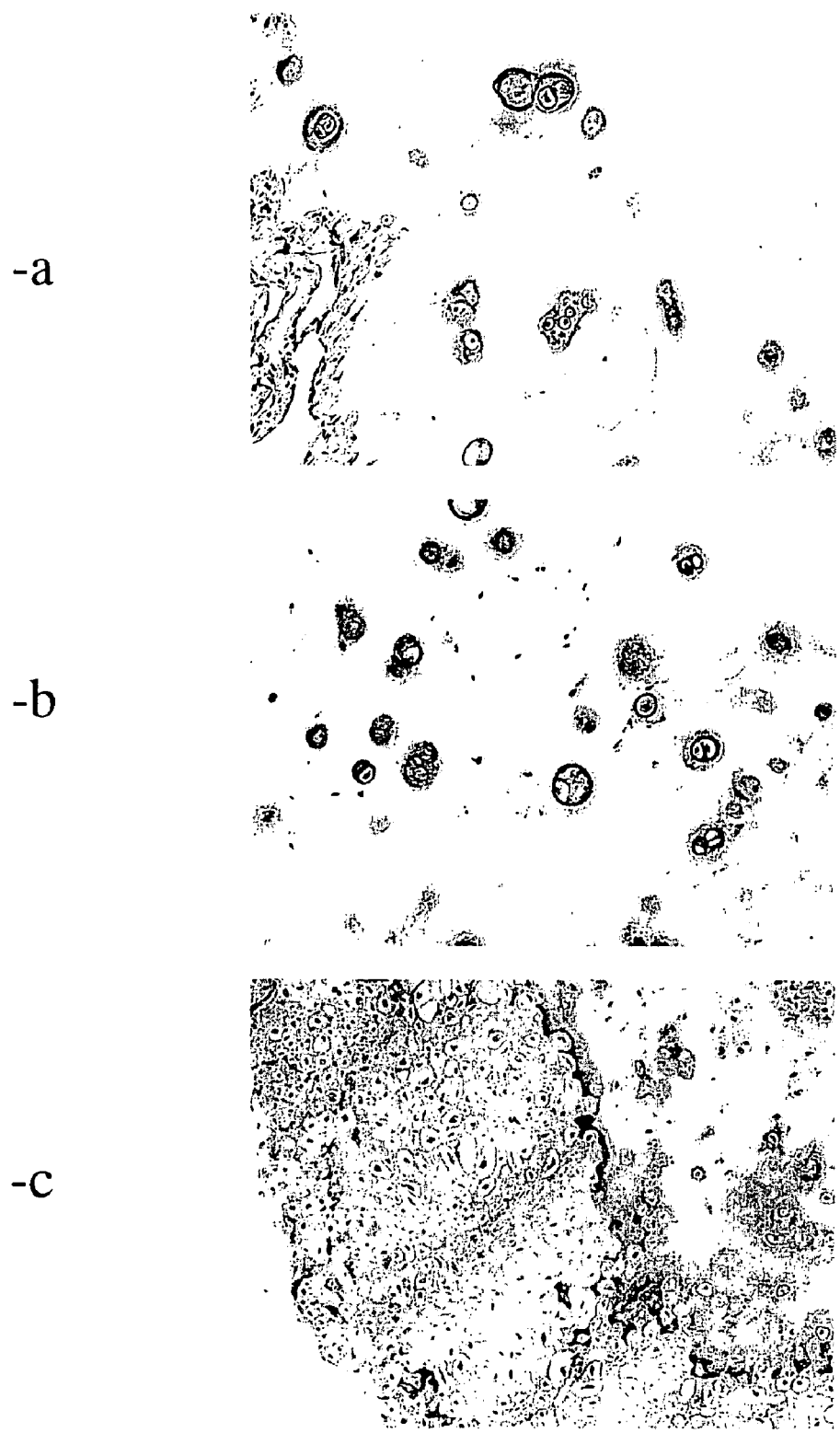
FIG. 4 shows the gelled-structure immunologically stained for type II collagen after the culture. a, b and c represent A group, B group and C group, respectively.

On the 21st day of the culture, specimens were fixed with 10% formalin, and stained with hematoxylin/eosin or alcian blue. In order to identify the presence of Type II collagen, an important substrate of the hyaline cartilage, the specimens were immunologically stained using an anti-human type II collagen antibody (Daiichi Fine Chemical Co., Ltd.). FIGS. 2a, 3a and 4a represent the A group, FIGS. 2b, 3b and 4b represent the B group and FIGS. 2c, 3c and 4c represent the C group.

By the staining studies with hematoxylin/eosin (FIGS. 2a, b and c) and with alcian blue (FIGS. 3a, b and c), a significant increase of the cell number was observed in the C group. In both stainings, the chondrocytes and cartilage spaces were observed, indicating the regeneration of the cartilage tissue. Meanwhile, many spindle body-shaped cells which were fibroblast-like were observed in the A group.

The immunological staining of collagen type II (FIGS. 4a, b and c) showed the appearance of collagen type II stained with brown color in peripheries of the chondrocytes. In addition, cytoplasmic portions were stained with brown color, suggesting the synthesis of collagen type II.

In the histological evaluation, the cells were identified to proliferate not in the center of the gel but in peripheries of the gel in common in all groups. Almost no alive cell was identified in the center of the gel in the A and B groups. In the C group, some alive cells were identified in the center of the gel compared with the A and B group. In the D group, the gel formation was poor, there seems to be a problem of the mixture ratio of collagen and proteoglycan, and thus the D group was not evaluated histologically.

Figure 5:
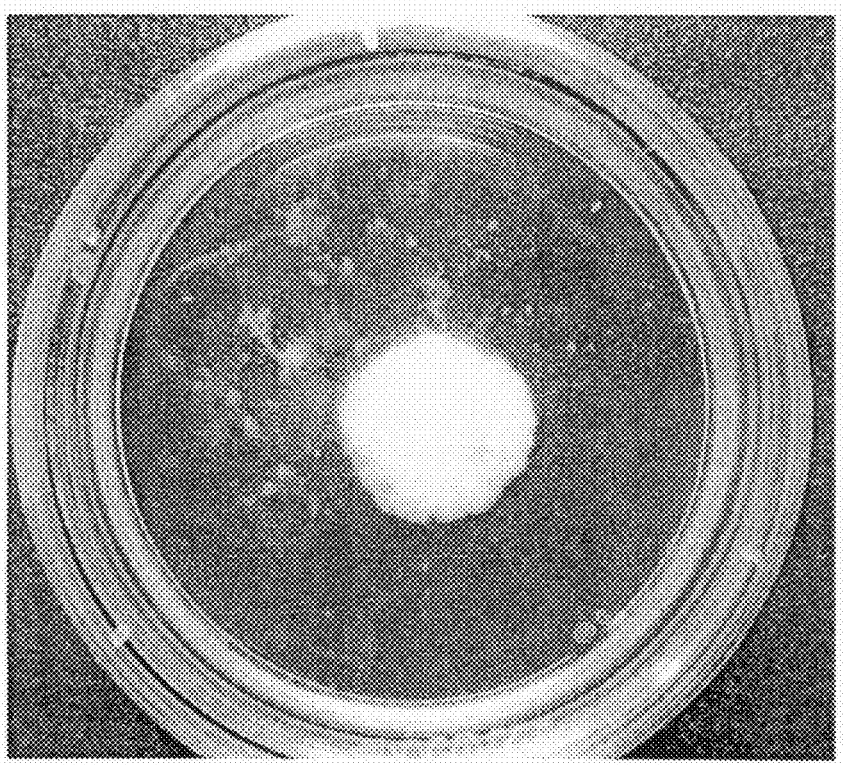
FIG. 5 is a photograph of the gelled structure (A group) on the 56th day of the culture using a digital camera.
Figure 6:
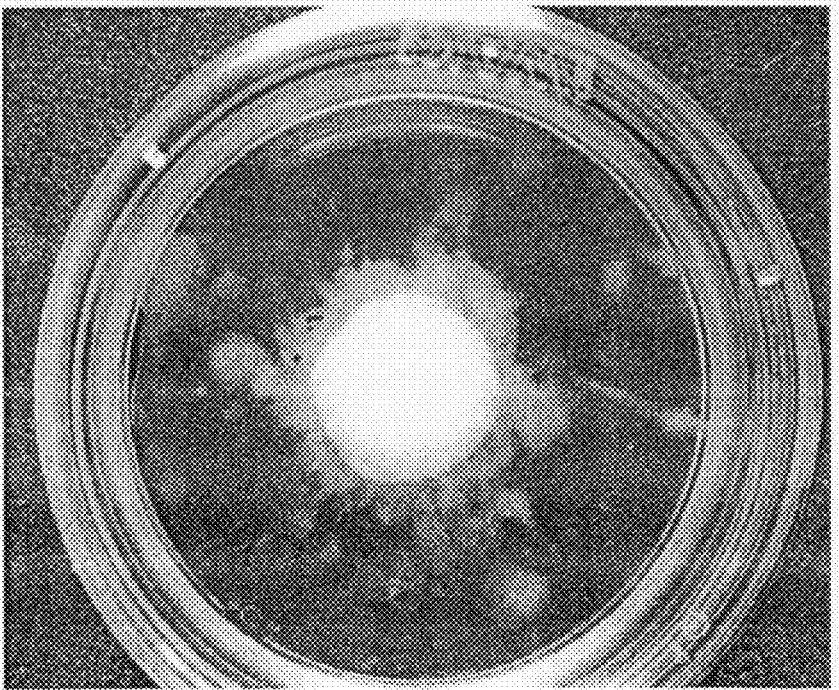
FIG. 6 is a photograph of the gelled structure (C group) on the 56th day of the culture using the digital camera.

FIGS. 5 (A group) and 6 (C group) show the cultured gel on the 56th day of the culture. In the A group, the gel tends to shrink and the shape begins to collapse. A phase contrast microscopic observation showed that the spindle-shaped cells were overlaid, speculating that the chondrocytes had altered to fibroblast-like cells. On the other hand, in the C group, the gel surface was smooth and the shape of the gel was kept well. The phase contrast microscopic observation showed that the circular cells were overlaid, indication that the chondrocytes proliferate with keeping their characters.

The invention claimed is:

1. A method for three-dimensional culture of chondrocytes, characterized by culture condition in which the chondrocytes are embedded in a gelled structure prepared by mixing collagen and proteoglycan, dropped on a culture dish and gelled, wherein a ratio of collagen to proteoglycan is 1:0.3 to 1:1.1 by weight, wherein the concentration of collagen is 0.8 to 2.4% by weight and the concentration of proteoglycan is 0.4 to 1.2% by weight, and wherein collagen is selected from the group consisting of atelocollagen and low molecular weight collagen hydrolyzed with enzyme.

2. A method of chondrocyte production characterized in that the chondrocytes are grown in a gelled structure prepared by mixing collagen and proteoglycan, dropped on a culture dish and gelled, wherein a ratio of collagen to proteoglycan is 1:0.3 to 1:1.1 by weight, wherein the concentration of collagen is 0.8 to 2.4% by weight and the concentration of proteoglycan is 0.4 to 1.2% by weight, and wherein collagen is selected from the group consisting of atelocollagen and low molecular weight collagen hydrolyzed with enzyme.

* * * * *